(12) United States Patent
Behler et al.

(10) Patent No.: US 9,931,286 B2
(45) Date of Patent: Apr. 3, 2018

(54) COSMETIC COMPOSITION COMPRISING ESTER OF LEVULINIC ACID WITH A FATTY ALCOHOL

(71) Applicant: BASF SE, Ludwigshafen (DE)

(72) Inventors: Ansgar Behler, Bottrop (DE); Laurence Pottie, Cologne (DE); Eva Max, Bayreuth (DE); Almud Folge, Solingen (DE); Monika Barbenheim, Bottrop (DE)

(73) Assignee: BASF SE, Ludwigshafen (DE)

( * ) Notice: Subject to any disclaimer, the term of this patent is extended or adjusted under 35 U.S.C. 154(b) by 18 days.

(21) Appl. No.: 15/104,553

(22) PCT Filed: Dec. 9, 2014

(86) PCT No.: PCT/EP2014/076986
§ 371 (c)(1),
(2) Date: Jun. 15, 2016

(87) PCT Pub. No.: WO2015/091091
PCT Pub. Date: Jun. 25, 2015

(65) Prior Publication Data
US 2016/0310381 A1 Oct. 27, 2016

(30) Foreign Application Priority Data
Dec. 19, 2013 (EP) .................... 13198352

(51) Int. Cl.
| | | |
|---|---|---|
| *A61K 8/37* | (2006.01) | |
| *A61K 8/19* | (2006.01) | |
| *A61K 8/44* | (2006.01) | |
| *A61K 8/34* | (2006.01) | |
| *A61K 8/46* | (2006.01) | |
| *A61Q 5/02* | (2006.01) | |
| *A61K 8/60* | (2006.01) | |
| *A61K 8/86* | (2006.01) | |
| *A61Q 19/10* | (2006.01) | |

(52) U.S. Cl.
CPC ............... *A61K 8/37* (2013.01); *A61K 8/19* (2013.01); *A61K 8/345* (2013.01); *A61K 8/44* (2013.01); *A61K 8/442* (2013.01); *A61K 8/463* (2013.01); *A61K 8/602* (2013.01); *A61K 8/86* (2013.01); *A61Q 5/02* (2013.01); *A61Q 19/10* (2013.01); *A61K 2800/262* (2013.01); *A61K 2800/48* (2013.01); *A61K 2800/596* (2013.01)

(58) Field of Classification Search
None
See application file for complete search history.

(56) References Cited

U.S. PATENT DOCUMENTS

| | | |
|---|---|---|
| 2,008,720 A | 7/1935 | Lawson et al. |
| 5,034,159 A | 7/1991 | Tesmann et al. |
| 2008/0110081 A1 | 5/2008 | Rae et al. |
| 2012/0101187 A1 | 4/2012 | Kuo et al. |

FOREIGN PATENT DOCUMENTS

| | | |
|---|---|---|
| DE | 2311675 A1 | 9/1974 |
| JP | 73043178 B | 5/1970 |
| JP | 2012131716 A | 7/2012 |
| WO | WO-2005/044960 A1 | 5/2005 |

OTHER PUBLICATIONS

Behler, A., et al., "Neue Verdickungsmitteln für Tensidformulierungen, New Thickening Agents for Surfactants," *SÖFW, Seifen, Öle, Fette, Wachse* (1990), vol. 116, No. 2, pp. 60-68.
Klinger, F. D., et al. (online data copyright 2012). "Oxocarboxylic Acids," chapter 4, "Levulinic Acid," *Ullmann's Encyclopedia of Industrial Chemistry*, Wiley-VCH Verlag GmbH & Co. KGaA, Weinheim Germany.
International Search Report for International Patent Application No. PCT/EP2014/076986, dated Feb. 18, 2015.

*Primary Examiner* — Bong-Sook Baek
(74) *Attorney, Agent, or Firm* — Marshall, Gerstein & Borun LLP

(57) ABSTRACT

The present invention relates to a composition comprising water, at least one surfactant, at least one ester of levulinic acid with a fatty alcohol and a water-soluble salt. Furthermore the present invention relates to the use of at least one ester of levulinic acid with a fatty alcohol for increasing the viscosity of a composition comprising water and at least one surfactant.

14 Claims, No Drawings

COSMETIC COMPOSITION COMPRISING ESTER OF LEVULINIC ACID WITH A FATTY ALCOHOL

CROSS-REFERENCE TO RELATED APPLICATIONS

This is the U.S. national phase of International Application No. PCT/EP2014/076986, filed Dec. 9, 2014, which claims the benefit of European Patent application No. 131983520, filed Dec. 19, 2013.

The present invention relates to a composition comprising water, at least one surfactant, at least one ester of levulinic acid with a fatty alcohol and a water-soluble salt. Furthermore the present invention relates to the use of at least one ester of levulinic acid with a fatty alcohol for increasing the viscosity of a composition comprising water and at least one surfactant.

Thickening agents, also called thickeners, are widely used in cosmetic formulations in order to adjust their viscosity to a desired level. An introduction to this topic is presented in "Seifen, Öle, Fette, Wachse, 116. Jg.—Nr. Feb. 1990", pages 60 to 68. In this publication it is disclosed that the viscosity of aqueous solutions of ionic surfactants can be increased by the addition of salts, e. g. sodium chloride, and/or by the addition of non-ionic low-molecular weight thickeners, e. g. fatty acid alkanolamides or fatty alcohol ethoxylates. It is also disclosed that the thickening effect of non-ionic low-molecular weight thickeners can be increased by adding salts, e. g. sodium chloride, whereby a maximum thickening effect is achieved at a specific salt concentration and whereby the thickening effect decreases if the salt concentration is increased further beyond said specific salt concentration.

U.S. Pat. No. 5,034,159 discloses the use of ethoxylated and/or propoxylated fatty alcohols as thickeners for aqueous surfactant solutions.

Levulinic acid and derivatives of levulinic acid are described in Ullmann's Encyclopedia of Industrial Chemistry (online database, copyright 2012, Wiley-VCH Verlag GmbH & Co. KGaA, Weinheim, Germany) in the article on oxocarboxylic acids, chapter 4 "levulinic acid". It is reported that levulinic acid esters (also called levulinates) are used in the production of cosmetics. In this context reference is made to "Y. Hikotaro, JP 73 43 178, 1973" (reference no. 47). This reference seems to be a typographical error. Japanese patent 480 43 178 which issued in 1973 with Y. Hikotaro as inventor and which can be found in other databases as Japanese patent no. 73 043 178, according to an abstract retrieved (abstract of the Derwent World Patent Index), discloses adhesive compounds containing levulinic acid.

U.S. Pat. No. 2,008,720 discloses the synthesis of levulinic acid esters of alcohols having from 7 to 18 carbon atoms. The use of the levulinic acid esters as plastisizers for cellulose derivatives is also disclosed.

WO 2005/044960 discloses the use of levulinates and in particular short chain levulinates (C4-C8 alkyl levulinate) as biofuel.

DE 2 311 675 A1 discloses levulinic acid esters having antimicrobial properties. Amongst other esters levulinic acid hexyl ester is disclosed. The use of said levulinic acid esters as antimicrobial agents in cosmetic applications and personal care applications is disclosed. It is disclosed that said levulinic acid esters may be applied in the form of solutions or creams which may contain anionic or nonionic surfactants. However, it is not disclosed that levulinic acid esters have a thickening effect. No synergistic thickening together with salts is disclosed. The combination of levulinic acid hexyl ester with amphoteric surfactants is disclosed.

JP 2012 131716 A, according to its English abstract (abstract of the Derwent World Patent Index), discloses a deodorizing aerosol product containing levulinic acid and its derivatives.

Many known non-ionic low-molecular weight thickeners, e. g. or fatty alcohol ethoxylates have the disadvantage that they are based on petrochemical raw materials. There is, however, an increasing demand for thickeners which are based on renewable raw materials.

The problem underlying the present invention is to provide a composition suitable for cosmetic applications comprising a thickening agent that is based on renewable raw materials.

Surprisingly it has been found that fatty alcohol esters of levulinic acid are useful as thickening agents in compositions suitable for cosmetic applications.

Levulinic acid is accessible by fermentation and is therefore based on renewable raw materials. Fatty acid moieties are also accessible based on renewable raw materials, e. g. based on oils of plant origin.

One subject of the present invention is a composition comprising water, at least one surfactant selected from the group consisting of an anionic surfactant, a cationic surfactant, an amphoteric surfactant, a nonionic surfactant and mixtures thereof, at least one ester of levulinic acid with a fatty alcohol, preferably a linear fatty alcohol, wherein the fatty alcohol has 6 to 22 C-atoms and a water-soluble salt, preferably an inorganic water-soluble salt. This composition is referred to as the composition according to the present invention.

One embodiment of the present invention ("embodiment 1") is the composition according to the present invention, with the proviso that when the at least one ester of levulinic acid with a fatty alcohol is levulinic acid hexyl ester, then the surfactant is not an amphoteric surfactant.

One embodiment of the present invention ("embodiment 2") is the composition according to the present invention or the composition according to embodiment 1, wherein the water-soluble salt is present in an amount of 1 to 10, preferably 1 to 5, more preferably 2 to 4, % by weight.

One embodiment of the present invention ("embodiment 3") is the composition according to the present invention or the composition according to any of embodiments 1 to 2, wherein the fatty alcohol has 8 to 22, preferably 8 to 18, C-atoms.

One embodiment of the present invention ("embodiment 4") is the composition according to the present invention or according to any of embodiments 1 to 3, wherein the at least one surfactant is selected from the group consisting of an anionic surfactant, a cationic surfactant and mixtures thereof.

One embodiment of the present invention ("embodiment 5") is the composition according to the present invention or according to any of embodiments 1 to 3, wherein the at least one surfactant is an anionic surfactant, preferably an anionic surfactant having a sulfate group or a sulfonate group or a carboxylate group.

One embodiment of the present invention ("embodiment 6") is the composition according to the present invention or the composition according to any of embodiments 1 to 5, wherein the salt is an alkali metal halide, preferably sodium chloride.

One embodiment of the present invention ("embodiment 7") is the composition according to the present invention or the composition according to any of embodiments 1 to 6, wherein the composition comprises 3 to 30, preferably 5 to 20, more preferably 6 to 15, % by weight surfactant, and 0.05 to 10, preferably 0.1 to 5, more preferably 0.2 to 3, % by weight ester of levulinic acid with a fatty alcohol, and water and optionally further ingredients suitable for use cosmetic compositions (ad 100% by weight).

One embodiment of the present invention ("embodiment 8") is the composition according to embodiment 7, wherein the composition comprises further ingredients suitable for use cosmetic compositions.

Another subject of the present invention is the use of at least one ester of levulinic acid with a fatty alcohol, preferably a linear fatty alcohol, wherein the fatty alcohol has 6 to 22, preferably 8 to 18, C-atoms, for increasing the viscosity of a composition comprising water, and at least one surfactant selected from the group consisting of an anionic surfactant, a cationic surfactant, an amphoteric surfactant, a nonionic surfactant and mixtures thereof.

One embodiment of the present invention is the use according to the previous paragraph, wherein the composition is the composition according to the present invention or the composition as defined in any of embodiments 1 to 8 as defined in the previous paragraphs and wherein the at least one ester of levulinic acid with a fatty alcohol is an ester of levulinic acid with a fatty alcohol as defined in any of embodiments 1 to 8 as defined in the previous paragraphs.

According to the present invention a fatty alcohol is an aliphatic alcohol having exactly one OH-group. This OH-group is a primary OH-group. The hydrocarbon moiety of the fatty alcohol has 6 to 22 carbon atoms. The hydrocarbon moiety of the fatty alcohol may be saturated or unsaturated, it may be linear or branched, it may not be cyclic. Preferably it is linear, more preferably it is linear and saturated.

The levulinic acid esters according to the present invention may be made according to the process disclosed in U.S. Pat. No. 2,008,720 which discloses the synthesis of levulinic acid esters of alcohols having from 7 to 18 carbon atoms.

In one embodiment of the present invention the at least one ester of levulinic acid with a fatty alcohol comprises or is levulinic acid octyl ester.

In one embodiment of the present invention the at least one ester of levulinic acid with a fatty alcohol comprises or is levulinic acid decyl ester.

In one embodiment of the present invention the at least one ester of levulinic acid with a fatty alcohol comprises or is levulinic acid dodecyl ester.

In one embodiment of the present invention the at least one ester of levulinic acid with a fatty alcohol comprises or is levulinic acid tetradecyl ester.

In one embodiment of the present invention the at least one ester of levulinic acid with a fatty alcohol comprises or is a mixture of levulinic acid octyl ester and levulinic acid decyl ester in a weight ratio of 1:4 to 4:1.

In one embodiment of the present invention the at least one ester of levulinic acid with a fatty alcohol comprises or is a mixture of levulinic acid dodecyl ester and levulinic acid tetradecyl ester in a weight ratio of 1:4 to 4:1.

According to the present invention the water-soluble salt is any water-soluble salt but is different from any of the surfactants comprised in the composition according to the present invention. In one embodiment of the present invention the water-soluble salt is an inorganic water-soluble salt. In one embodiment of the present invention the water-soluble salt is an alkali metal halide, preferably sodium chloride. "Water-soluble" means that the salt is soluble at 20° C. in the composition according to the present invention in the amount in which the salt is used.

Alternatively, water-soluble salts include any water-soluble alkali metal, ammonium and alkaline earth salts, for example the fluorides, chlorides, bromides, sulfates, phosphates, nitrates, providing they are soluble in water in a quantity of at least 1% by weight at a temperature of 20° C. The chlorides or sulfates of an alkali metal, ammonium or magnesium are preferably used. Sodium chloride and magnesium chloride are particularly preferred.

Particularly suitable organic electrolyte salts include any water-soluble alkali, ammonium and alkaline metal earth salts of mono-, di- and tricarboxylic acids. Preference is attributed to carboxylic acids having a molecular weight less than 200 g/mol, for example succinic acid, tartaric acid and glutaric acid. Mixtures of these salts may also be used in accordance with the invention.

The anionic surfactant according to the present invention can be any anionic surfactant.

Anionic surfactants which may be used as surfactant according to the present invention are characterized by a water-solubilizing, anionic group, for example a carboxylate, sulfate, sulfonate or phosphate group and a lipophilic radical. Skin-compatible anionic surfactants are known to the person skilled in the art in a large number from relevant handbooks and are commercially available. These are especially alkyl sulfates in the form of their alkali metal, ammonium or alkanolammonium salts, alkyl ether sulfates, alkyl ether carboxylates, acyl isethionates, acyl sarcosinates, acyltaurines with linear alkyl or acyl groups having 12 to 18 carbon atoms, and also sulfosuccinates and acyl glutamates in the form of their alkali metal or ammonium salts.

Typical examples of anionic surfactants are soaps, alkylbenzenesulfonates, alkanesulfonates, olefinsulfonates, alkyl ether sulfonates, glycerol ether sulfonates, α-methyl ester sulfonates, sulfo fatty acids, alkyl sulfates, fatty alcohol ether sulfates, glycerol ether sulfates, fatty acid ether sulfates, hydroxy mixed ether sulfates, monoglyceride (ether) sulfates, fatty acid amide (ether) sulfates, mono- and dialkyl sulfosuccinates, mono- and dialkyl sulfosuccinamates, sulfo-triglycerides, amide soaps, ethercarboxylic acids and salts thereof, fatty acid isethionates, fatty acid sarcosinates, fatty acid taurides, N-acylamino acids, for example acyl lactylates, acyl tartrates, acyl glutamates and acyl aspartates, alkyl oligoglucoside sulfates, protein fatty acid condensates (especially vegetable products based on wheat) and alkyl (ether) phosphates. If the anionic surfactants comprise polyglycol ether chains, these may have a conventional homolog distribution, but preferably have a narrow homolog distribution.

The cationic surfactant according to the present invention can be any cationic surfactant.

Cationic surfactants which may be used as surfactant according to the present invention are especially quaternary ammonium compounds. Preference is given to ammonium halides, especially chlorides and bromides, such as alkyltrimethylammonium chlorides, dialkyldimethylammonium chlorides and trialkylmethylammonium chlorides, e.g. cetyltrimethylammonium chloride, stearyl-trimethylammonium chloride, distearyl-dimethylammonium chloride, lauryldimethylammonium chloride, lauryldimethylbenzylammonium chloride and tricetylmethylammonium chloride. In addition, the very readily biodegradable quaternary ester compounds, for example the dialkylammonium methosulfates and methylhydroxyalkyldialkyloxyalkylammonium methosulfates sold under the trade name Stepantex® and the corresponding products of the Dehyquart® series can also be used as cationic surfactants. The term "ester quats" are generally understood to mean quaternized fatty acid triethanolamine ester salts. They can impart an exceptional soft feel to the preparations according to the invention. These are known substances which are prepared by the relevant methods of organic chemistry. Further cationic surfactants which can be used in accordance with the invention are the quaternized protein hydrolyzates.

The amphoteric surfactant according to the present invention can be any amphoteric surfactant. According to the present invention, amphoteric surfactants shall also comprise zwitterionic surfactants.

Amphoteric surfactants (also referred to as ampholytic surfactants in the following text) which may be used as surfactant according to the present invention are surface-active compounds which, apart from a $C_8$-$C_{18}$-alkyl or acyl group in the molecule, contain at least one free amino group and at least one —COOH or —$SO_3H$ group and are capable of forming internal salts. Examples of suitable ampholytic surfactants are N-alkylglycines, N-alkylpropionic acids, N-alkylaminobutyric acids, N-alkyliminodipropionic acids, N-hydroxyethyl-N-alkylamidopropylglycines, N-alkyltaurines, N-alkyl-sarcosines, 2-alkylaminopropionic acids and alkylaminoacetic acids having in each case about 8 to 18 carbon atoms in the alkyl group. Particularly preferred ampholytic surfactants are N-coco-alkylaminopropionate, cocoacylaminoethylaminopropionate and $C_{12-18}$-acylsarcosine.

Typical examples of amphoteric or zwitterionic surfactants which may be used as surfactant according to the present invention are alkylbetaines, alkylamidobetaines, aminopropionates, aminoglycinates, imidazolinium betaines and sulfobetaines. The specified surfactants are exclusively known compounds. With regard to the structure and preparation of these substances, reference may be made to relevant review works in this field. Typical examples of particularly suitable mild, i.e. particularly skin-friendly, surfactants are fatty alcohol polyglycol ether sulfates, monoglyceride sulfates, mono- and/or dialkyl sulfosuccinates, fatty acid isethionates, fatty acid sarcosinates, fatty acid taurides, fatty acid glutamates, α-olefinsulfonates, ether carboxylic acids, alkyl oligoglucosides and/or mixtures thereof with alkyl oligoglucoside carboxylates, fatty acid glucamides, alkylamidobetaines, amphoacetals and/or protein fatty acid condensates, the latter preferably based on wheat proteins or salts thereof.

The compositions according to the present invention may additionally comprise further cosmetic ingredients. They may contain perfumes, dyes, opacifiers and pearlescers, antimicrobial agents, preservatives, skin-emollient agents, plant extracts, protein hydrolyzates, buffers, complexing agents and other known auxiliaries and additives of the type normally present in shampoos, bath additives, shower bath preparations, liquid soaps, liquid skin cleansers, liquid hair rinses, and also in liquid laundry and dishwashing detergents and liquid domestic cleaning preparations based on ionic surfactants.

The compositions according to the present invention may comprise polymers that are commonly used in cosmetic compositions, e. g., but not limited to, polymeric thickening agents. It is preferred that the compositions according to the present invention comprise not more than 30% by weight polymers, more preferably not more than 20% by weight polymers, more preferably not more than 10% by weight polymers.

The composition according to the present invention may be used in cosmetic formulations such as shower gels, shampoos, bubble baths, hand washing formulations, or in home care formulations, like for instance dishwashing liquid, house cleaning products, degreasing formulations and the like. The composition may also be used in any other applications where thickening of a surfactant solution is of advantage. This may include agricultural, coatings and surface treatment applications, oil recovery or mining applications, or applications in the construction area.

The compositions according to the present invention have many beneficial properties. It is possible to obtain the compositions according to the present invention in clear, optically transparent form. The compositions according to the present invention have good foaming properties. The viscosities that can be achieved when the levulinic acid esters according to the present invention are used in combination with a salt are even higher than the ones measured using Arlypon® F (an ethoxylated fatty alcohol). Therefore to reach the desired viscosity salts, e. g. NaCl can be used, which is also beneficial to increase the mildness of the formulation. It is assumed that the compositions according to the present invention have antimicrobial properties. They have good cleansing properties. They are based on natural raw material obtainable from renewable resources.

EXAMPLES

Synthesis Examples

Materials:
Fatty alcohols of various chain length compositions were used, which are commercially available under the trademark "Lorol®". The chain length distribution is as follows:

TABLE 1

Carbon chain length distribution of the commercially available fatty alcohols used for the levulinate synthesis

| Trademark | C Chain | Specification [%] |
|---|---|---|
| Lorol ® $C_8$-98 | $C_6$ | 0-1 |
| | $C_8$ | 98 (min) |
| | $C_{10}$ | 0-2 |
| Lorol ® $C_8$-$C_{10}$ Spezial | $C_6$ | 0-1 |
| | $C_8$ | 40-48 |
| | $C_{10}$ | 51-59 |
| | $C_{12}$ | 0-1 |
| Lorol ® $C_{10}$-98 | $C_8$ | 0-2 |
| | $C_{10}$ | 98 (min) |
| Lorol ® $C_{12}$-$C_{14}$ Spezial | $C_{10}$ | 0-2 |
| | $C_{12}$ | 65-71 |
| | $C_{14}$ | 22-28 |
| | $C_{16}$ | 4.0-5.5 |
| | $C_{18}$ | 0.0-0.5 |
| Lorol ® $C_{12}$-98 | $C_{10}$ | 0-2 |
| | $C_{12}$ | 98 (min) |
| | $C_{14}$ | 0-2 |
| HD-Ocenol ® 90/95 V (C18:1-Levulinate) | $C_{14}$ | 0-2.0 |
| | $C_{16}$ | 2.0-10 |
| | $C_{18}$ | 90-98 |
| | $>C_{18}$ | 0.0-3.0 |

Levulinic acid with a purity of at least 97% was used.
Synthesis:
The fatty alcohol, levulinic acid (in a 1:1 molar ratio) and a catalyst such as methane sulfonic acid were placed in a glass reactor under an inert atmosphere. The mixture was slowly heated up while continuously stirring until water distilled off, vacuum was applied to facilitate and accelerate water removal. In case a fatty alcohol excess was used, the residual alcohol was also distilled off. After the water was distilled off the reaction medium was cooled down to room temperature. The hydroxyl values (measured by the acetic acid method), saponification values (determined according to ISO 3657:2002) and acid values (determined according to ISO 660:1996) of the products obtained are summarized in table 2.

In the tables below the levulinate esters are referred to as Cx-levulinate, where Cx stands for the fatty alcohol carbon chain length. Cx/y stand for mixtures of fatty alcohols of x and y carbons. Unless specified otherwise a molar ratio alcohol:acid of 1:1 was used for the synthesis.

TABLE 2

Analytics of the levulinic acid esters

| Structure | Hydroxyl Value [$mg_{KOH}/g$] | Acid Value [$mg_{KOH}/g$] | Saponification Value [$mg_{KOH}/g$] |
|---|---|---|---|
| $C_8$ Levulinate | 0.55 | 1.54 | 242.3 |
| $C_{10}$ Levulinate | 0.08 | 0.88 | 217.8 |
| $C_{8/10}$ Levulinate | 14.7 | 1.8 | 214.1 |
| $C_{12}$ Levulinate | 7.1 | 8.9 | 198 |
| $C_{12/14}$ Levulinate | 4.6 | 3.9 | 190.2 |
| $C_{18:1}$ Levulinate | 6.44 | 1.62 | 152.4 |

Application Examples: Thickening of Water-Based Cosmetic Formulations

The individual components were weighed and mixed together in a water bath (all given percentages are weight-percentages). After the formulations were bubble-free and air-conditioned, the viscosity was determined using the Brookfield viscometer II+D pro (Spindel S64).

TABLE 3

Viscosity of formulations containing: 9% Texapon ® N (INCI: Sodium Laureth Sulfate); 3% Dehyton ® PK 45 (INCI: Cocamidopropyl Betaine 2% NaCl; x % thickener, measured with 1.5 rpm.

| Structure | Concentration [%] | Appearance of formulation | Viscosity [mPas] |
|---|---|---|---|
| Arlypon ® F (lauryl ethoxylate) | 0.4 | Clear | 49 989 |
|  | 1.0 | Clear | 142 000 |
| $C_{12}$ Levulinate | 0.4 | Clear | 75 384 |
|  | 1.0 | Clear | 175 000 |
| $C_{12/14}$ Levulinate | 0.1 | Clear | 36 392 |
|  | 0.2 | Clear | 59 987 |
|  | 0.4 | Clear | 94 380 |
|  | 1.0 | Clear | 260 000 |
| $C_{10}$ Levulinate | 1.0 | Clear | 83 182 |
| $C_{8/10}$ Levulinate | 1.0 | Clear | 45 990 |
| $C_8$ Levulinate | 1.0 | Clear | 54 388 |
| $C_{18:1}$ Levulinate | 1.0 | Clear | 208 000 |

TABLE 4

Viscosity of formulations containing: 12% Plantapon ® SF (INCI: Sodium Cocoamphoacetate (and) Glycerin (and) Lauryl Glucoside (and) Sodium Cocoyl Glutamate (and) Sodium Lauryl Glucose Carboxylate); 1.0% thickener, measured with 60.0 rpm.

| Structure | Concentration [%] | Appearance | Viscosity [mPas] |
|---|---|---|---|
| Arlypon ® F | 1.0 | Clear | 2 190 |
| $C_{12/14}$ Levulinate | 1.0 | Clear | 4 829 |

TABLE 5

Viscosity of formulations containing: 9% Texapon ® N (INCI: Sodium Laureth Sulfate); 3% Dehyton ® PK 45 (INCI: Cocamidopropyl Betaine); x % NaCl; 0.4 or 0.2% thickener, measured at 1.5 rpm.

| Thickener [%] | NaCl [%] | Appearance | Viscosity [mPas] |
|---|---|---|---|
| Arlypon ® F [0.4%] | 0 | Clear | <100 |
|  | 1 | Clear | 1 067 |
|  | 2 | Clear | 56 000 |
|  | 3 | Clear | 136 000 |
|  | 4 | Clear | 74 660 |
|  | 5 | Clear | 8 000 |
| $C_{12}$ Levulinate [0.4%] | 0 | Clear | <100 |
|  | 1 | Clear | 2 399 |
|  | 2 | Clear | 102 000 |
|  | 3 | Clear | 183 000 |
|  | 4 | Clear | 83 582 |
|  | 5 | Clear | 3 199 |
| $C_{12/14}$ Levulinate [0.4%] | 0 | Clear | <100 |
|  | 1 | Clear | 400 |
|  | 2 | Clear | 83 982 |
|  | 3 | Clear | 178 000 |
|  | 4 | Clear | 45 590 |
|  | 5 | Clear | 800 |

TABLE 6

Viscosity of formulations containing: 9% Texapon ® N (INCI: Sodium Laureth Sulfate); 3% Dehyton ® PK 45 (INCI: Cocamidopropyl Betaine); x % NaCl; 0.2% thickener, measured at 1.5 rpm.

| Thickener [%] | NaCl [%] | Appearance | Viscosity [mPas] |
|---|---|---|---|
| Arlypon ® F [0.2%] | 0 | Clear | <100 |
|  | 1 | Clear | <100 |
|  | 2 | Clear | 38 792 |
|  | 3 | Clear | 150 000 |
|  | 4 | Clear | 155 000 |
|  | 5 | Clear | 54 388 |
| $C_{12/14}$ Levulinate [0.2%] | 0 | Clear | <100 |
|  | 1 | Clear | 400 |
|  | 2 | Clear | 59 987 |
|  | 3 | Clear | 169 000 |
|  | 4 | Clear | 138 000 |
|  | 5 | Clear | 65 186 |

The invention claimed is:

1. A composition comprising
water,
at least one surfactant selected from the group consisting of an anionic surfactant, a cationic surfactant, an amphoteric surfactant, a nonionic surfactant and mixtures thereof,
at least one ester of levulinic acid with a fatty alcohol, wherein the fatty alcohol has 6 to 22 C-atoms,
and a water-soluble salt wherein the water-soluble salt is an alkali metal halide.

2. The composition according to claim 1, with the proviso that when the at least one ester of levulinic acid with a fatty alcohol is levulinic acid hexyl ester, then the surfactant is not an amphoteric surfactant.

3. The composition according to claim 1, wherein the water-soluble salt is present in an amount of 1 to 10% by weight.

4. The composition according to claim 1, wherein the fatty alcohol has 8 to 22 C atoms.

5. The composition according to claim 1, wherein the at least one surfactant is selected from the group consisting of an anionic surfactant, a cationic surfactant and mixtures thereof.

6. The composition according to claim 1, wherein the at least one surfactant is an anionic surfactant.

7. The composition according to any of claim 1, wherein the composition comprises
water,
3 to 30% by weight surfactant,
0.05 to 10% by weight ester of levulinic acid with a fatty alcohol wherein the fatty alcohol has 6 to 22 C-atoms,
a water-soluble salt wherein the water-soluble salt is an alkali metal halide, and
optionally further ingredients suitable for use in cosmetic compositions (add 100% by weight).

8. The composition according to claim 7, wherein the composition comprises further ingredients suitable for use in cosmetic compositions.

9. A method for increasing the viscosity of a composition comprising water and at least one surfactant selected from the group consisting of an anionic surfactant, a cationic surfactant, an amphoteric surfactant, a nonionic surfactant and mixtures thereof, comprising adding at least one ester of levulinic acid with a fatty alcohol wherein the fatty alcohol has 6 to 22 C-atoms and a water-soluble salt wherein the water-soluble salt is an alkali metal halide to the composition comprising water and at least one surfactant selected from the group consisting of an anionic surfactant, a cationic surfactant, an amphoteric surfactant, a nonionic surfactant and mixtures thereof.

10. The composition according to claim 1 wherein the fatty alcohol is a linear fatty alcohol.

11. The composition according to claim 4 wherein the fatty alcohol has 8 to 18 C-atoms.

12. The composition according to claim 6 wherein the anionic surfactant has a sulfate group or a sulfonate group or a carboxylate group.

13. The composition according to claim 1 wherein the alkali metal halide is sodium chloride.

14. The composition according to claim 7 wherein the composition comprises
water,
5 to 20% by weight surfactant,
0.1 to 5% by weight ester of levulinic acid with a fatty alcohol wherein the fatty alcohol has 6 to 22 C-atoms,
a water-soluble salt wherein the water-soluble salt is an alkali metal halide, and
optionally further ingredients suitable for use in cosmetic compositions (add 100% by weight).

* * * * *